United States Patent [19]

Tanaka et al.

[11] Patent Number: 4,501,734
[45] Date of Patent: Feb. 26, 1985

[54] PROMOTION OF ABSORPTION OF DRUGS ADMINISTERED THROUGH THE ALIMENTARY SYSTEM

[75] Inventors: Osamu Tanaka; Noboru Yata, both of Hiroshima, Japan

[73] Assignee: Wakunaga Yakuhin Kabushiki Kaisha, Japan

[21] Appl. No.: 354,289

[22] Filed: Mar. 3, 1982

[30] Foreign Application Priority Data

Mar. 6, 1981 [JP] Japan .................. 56-32012
Sep. 30, 1981 [JP] Japan ................. 56-155731

[51] Int. Cl.³ ...................... A01N 31/00; A01N 65/00
[52] U.S. Cl. .................................. 514/198; 424/195.1
[58] Field of Search ................ 536/18.1; 424/180, 195

[56] References Cited

U.S. PATENT DOCUMENTS 3,911,097  8/1973  Hanson ................................. 424/88
3,924,004 12/1975  Chang et al. ....................... 424/358
4,146,615  1/1978  Fauran et al. ....................... 424/180
4,335,113  5/1980  Combier et al. .................... 536/18.1

OTHER PUBLICATIONS

Chem. Abst., 73:77544v, (1970).
Chem. Abst., 73:110062m, (1970).
Chem. Abst., 73:110071p, (1970).
Chem. Abst., 74:13384f, (1971).
Chem. Abst., 85:106644h, (1975).
Encarnacion et al., Phytochemistry, vol. 20, No. 8, pp. 1939-1942, 1981.
Higuchi et al., Chem. Pharm. Bull. 24(5), 1021-1032, (1976).
Tori et al., Tetrahderon Letters, No. 46, pp. 4167-4170, 1976.
Ishii et al., Tetrahedron Letters, No. 14, pp. 1227-1230, 1977.

Primary Examiner—Sidney Marantz
Assistant Examiner—Shawn P. Foley
Attorney, Agent, or Firm—Wenderoth, Lind & Ponack

[57] ABSTRACT

An extract from a saponin-containing galenical has the effect of promoting absorption of a pharmacologically active substance or drug such as β-lactam antibiotic administered through the alimentary system. In particular, saponin components are isolated from the extract of *Sapindus mukurossi* Gaertn. and recognized to have similar promotion effect of drug absorption. Thus, it has been made possible to increase absorption of a drug and hence its pharmacological effect by administering these substances in combination with a pharmacologically active substance orally or into the rectum.

6 Claims, No Drawings

PROMOTION OF ABSORPTION OF DRUGS ADMINISTERED THROUGH THE ALIMENTARY SYSTEM

BACKGROUND OF THE INVENTION

1. Field of the Art

This invention relates to a saponin-containing galenical extract and a product isolated therefrom and more particularly to an absorption adjuvant composition for aiding adsorption of drugs to be absorbed or administered through the alimentary system. This invention is based on a finding relating to the pharmacological characteristics of this galenical extract capable of aiding, particularly promoting, absorption of a pharmacologically active substance administered through or into the alimentary system, e.g., orally or by insertion into the rectum.

2. Prior Art

Because of the difficulty in isolation by purification of saponin and its complicated structure, it has not been very long ago, only about ten and some years ago, when marked progress in research on saponin appeared.

As typical characteristics of saponins, they foam when shaken with water, act as powerful hemolytics by dissolving red blood corpuscles, are poisonous toward fish, and can form complexes with cholesterol (a steroid). As pharmaceuticals, they have been found to have pharmacological activities such as expectorant, antibechic, antiinflammatory, central nervous system blocking, antifatigue, antiulcer, cholesterol metabolism promoting, lipid metabolism promoting and nucleic acid or protein synthesis promoting activities. In addition, it has also recently been found that they have anti-infective and antitumor activities. Saponin-containing galenicals with relatively higher saponin contents listed in the Japanese Pharmacopoeia may include Senega, Polygala Root, Platycodon Root, Glycyrrhiza, Achyranthes Root, Bupleurum Root, Panax Rhizome, Ginseng, Ophiopogon Tuber, Akebia Stem, etc.

Saponins can be classified according to the chemical structures of the sapogenin or aglycone moieties thereof into steroid saponins and triterpenoid saponins. Triterpenoid saponins containing hederagenin as aglycone are obtained from various plants such as *Akebia guinata* Decne. (Chem, Pharm, Bull. 24, 1021 (1976)), *Caulophyllum robustum* Maxim. (C.A. 85, 106644h (1976), *Fatsia japonica.* Decne. (Phytochemistry 15, 781 (1976)), *Sapindus mukurossi* Gaertn. (C.A. 73, 77544, 110062m, 110071p (1970) and C.A. 74, 13384f (1971)), *Lecaniodiscus cupanioides* Planch. ex Benth (Phytochemistry 20, 1939 (1981)). But no systematic pharmacological research has been developed so far. Bupleurum root saponin, which is one of triterpenoid saponins, has very potent hemolytic and local excitory actions, exhibiting sedative, antalgic, hypothermal, antipyretic actions and anti-inflammatory effect, and it is also effective for digestive ulcer. As for a saponin from the peels of *Sapindus mukurossi* Gaertn., which is another triterpenoid saponin, it has not previously been used for medical purpose, but investigations about its anti-inflammatory action have been made due to similarlity in chemical structure. There is a report that it exhibited inhibitory effect in carragheenin edema and adjuvant arthritis of rats.

In spite of discovery of various pharmacological activities of saponin as mentioned above, systematic pharmacological research has just begun, and it can be expected in the future that a novel pharmacological effect not known in pharmaceuticals of prior art will be discovered.

On the other hand, in the administration of an antibacterial preparation, there is known the concept of minimal effective concentration in blood. At a level lower than such concentration, a drug is not effective even if it may exist persistently for a long time in a body. For this reason, the utilization percentage by absorption of a drug to be absorbed through the alimentary system is very important, and there have heretofore been investigations on methods for maintaining effective concentrations in blood with smaller amounts of drugs by enhancement of the absorption efficiency of drugs from the standpoint of either preparation or administration technique.

However, it would be greatly beneficial, if the absorption utilization percentage could be enhanced by administration of a conventional drug for oral administration according to a conventional oral administration method.

SUMMARY OF THE INVENTION

An object of the present invention is to provide an expendient for solving the above problem. This object has been achieved by the use of a saponin-containing galenical extract or a product isolated therefrom as an absorption adjuvant composition.

Thus, the adsorption adjuvant composition for a drug to be absorbed through the alimentary system according to the present invention, which is useful for aiding absorption of a pharmacologically active substance administered through or into the alimentary system, comprises a saponin-containing galenical extract or an isolated product therefrom and, optionally, a pharmaceutically acceptable vehicle.

In a specific embodiment of the invention, the isolated product has the form of a triterpenoid saponin represented by the following formula.

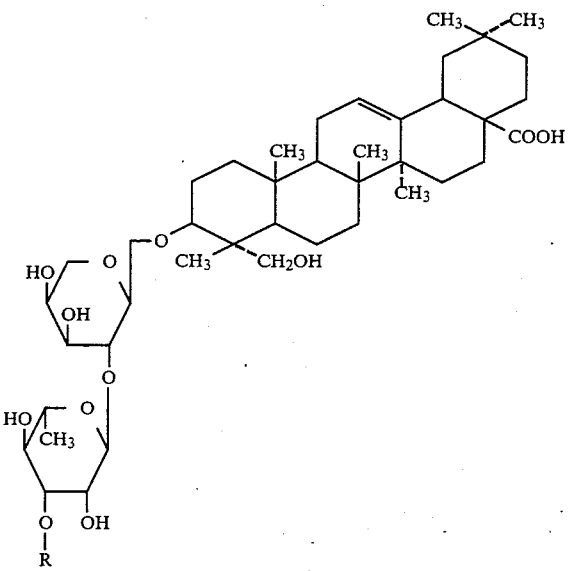

wherein R is

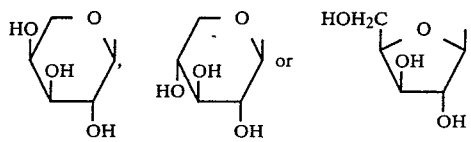

These triterpenoid saponins can be obtained by subjecting the peels of Sapindus mukurossi Gaertn. (hereinafter referred to as mukurossi peel), without or after defatting treatment, to extraction with a lower aliphatic alcohol or a mixture of water with a lower aliphatic alcohol and further separating the triterpenoid saponin represented by the above formula from the resulting extract fractions.

According to the present invention in another aspect thereof, there is also provided a pharmaceutical composition for administration through the alimentary system, comprising a combination of a safe and effective quantity of a saponin-containing galenical extract or a product isolated therefrom and a safe and effective amount of a pharmacologically active substance.

Further, the present invention also provides a method of administering through the alimentary system a pharmacologically active substance improved in absorption property, which comprises administering a pharmacologically active substance in combination with a saponin-containing galenical extract or a product isolated therefrom through alimentary system, especially, orally or into the rectum.

DETAILED DESCRIPTION OF THE INVENTION

1. Galanical extract

The galenical extract utilized in the present invention is an extract of a galenical containing a saponin component.

(1) Galenical

A large number of galenicals containing saponin components are known in the art, and any one of them can be employed in the present invention.

Typical examples of galenicals containing saponin components suitable for use in the present invention are enumerated below. In the present invention, the term "galenical" is used with the same meaning as or interchangeably with the corresponding "plant".

(1) (Pharm.) *Akebia quinata* Decne. or plants belonging to the same family (Lardizabalaceae).
(2) *Fatsia japonica* Decne. et Pianch.
(3) *Caulophyllum robustum* Maxim.
(4) *Hedera rhombea* Bean.
(5) *Clematis chinensis* Osbeck.
(6) *Pulsatilla cernua* Spreng.
(7) *Sapindus mukurossi* Gaertn.
(8) (Pharm.) *Panax japonicum* C. A. Meyer.
(9) (Pharm.) *Glycyrrhiza glabra* L. var. glandulifera Regel et Herder, *Glycyrrhiza uralensis* Fisher or plants belonging to the same family (Leguminosae).
(10) (Pharm.) *Polygala senega* L. or *Polygala senega* L. var. Latifolia Torrey et Gray.
(11) (Pharm.) *Platycodon grandiflorum* A.D.C.
(12) (Pharm.) *Polygala tenuifolia* Willd.
(13) (Pharm.) *Achyranthes fauriei* Lev. et Van or *Achyranthes bidentata* Blume.
(14) *Cyclamen europaeum*.
(15) *Primula officinalis*.
(16) (Pharm.) *Bupleurum falcatum* L. or its varieties (Umbelliferae).
(17) (Pharm.) *Panax ginseng* C. A. Meyer.
(18) *Panax notoginseng* Burkill.
(19) *Panax quinquefolium* L.

Remarks (1) Plants 1-7 contain saponins containing hederagenin as aglycone.
(2) A plant designated (Pharm.) is an original plant giving galenical listed in the Japanese Pharmacopoeia, 9th Edition.
(3) Root of Bupleurum falcatum L. is hereinafter referred to as Bupleurum root. This Bupleurum root and the mukurossi peel are famous galenicals from olden times.

(2) Extraction

The saponin-containing galenical extract to be utilized in the present invention can be obtained according to a conventional method using the above plants as starting materials from the galenicals thereof. That is, for example, the starting galenical, without being defatted or after being defatted with a conventional lipid-soluble organic solvent, is subjected to extraction of its effective ingredients with an extracting reagent such as water, a lower aliphatic alcohol, especially $C_1$–$C_4$ monohydric alcohol, or a mixture of water with a lower aliphatic alcohol. In addition to these extracting reagents, there may also be used a lower ketone such as acetone, a lower ether such as diethylether, an ester of a lower mono-carboxylic acid with a lower alcohol such as ethyl acetate and others.

In the present invention, the extract can be utilized as such or after concentration. Ordinarily, however, it is subjected to purification to some extent before use. According to one example of purification, the concentrated extract is suspended in water, the suspension with addition of n-butanol is shaken and, after separation of the n-butanol layer, the aqueous layer is evaporated to dryness.

The plants are not necessarily required to be naturally occurring; a product obtained by tissue culture of cells from the starting plant may also be employed. When the tissue cultured product is still in the undifferentiated state but already contains saponin components, it is also possible to apply an extraction operation on such a cultured product.

(3) Extract

The thus prepared extract contains saponin components.

The saponins contained in the extract to be used in the present invention have chemical structures which have not yet completely been elucidated. The critical specific feature which must be possessed commonly by the extracts of the present invention is that each must be an n-butanol-soluble component of a galanical containing a saponin and has an absorption promoting capability with respect to a pharmacologically active substance for oral administration.

The isolated mukurossi peel saponins have chemical structures (four kinds corresponding to four types of sugar moieties respectively bonded to hederagenin) as reported by us in "Abstracts of Lectures in 101th Annual Symposium of Pharmacological Society of Japan", and the use thereof as drug absorption aids is one embodiment of the present invention as will be described in detail hereinafter. The Bupleurum root saponin has a chemical structure as reported in J. C. S. Perkin I, 2043

(1975), Tetrahedron Letters No. 46, 4167 (1976) and Tetrahedron Letters No.14, 1227 (1977). The mukurossi peel saponins prepared by the present inventors are substances all in the form of white powders, irrespective of the difference in the sugar moieties, which are readily soluble in methanol and hardly soluble in water. On the other hand, the Bupleurum root saponins (including Bupleurum root saponins, a, c, d and etc.) are hygroscopic substances in the form of brown powders, which are readily soluble in methanol and hardly soluble in water.

The term "extract" as used herein refers comprehensively to both the extract in the state of a solution and the solid or powders obtained therefrom by removal of the solvent (that is, substantially saponin).

2. Isolated saponin product

The isolated mukurossi peel saponins as one embodiment of the isolated saponin products of the present invention include the three kinds of saponins A, B and C, depending on the kinds of R in the above formula, as shown below.

| Saponin | R |
|---|---|
| A | (sugar structure with HO, OH, OH) |
| B | (sugar structure with HO, OH, OH) |
| C | (sugar structure with HOH$_2$C, OH, OH) |

(1) Saponin A

Saponin A is a known substance (Phytochemistry, 20, 1939 (1981). That is, Saponin A is 3-O-[α-L-arabinopyranosyl-(1→3)-α-L-rhamnopyranosyl-(1→2)-α-L-arabinopyranosyl]-hederagenin.

(2) Saponin B

Saponin B is a known substance (C. A. 73, 77544v (1970)). That is, Saponin B is 3-O-[β-D-xylopyranosyl-(1→3)-α-L-rhamnopyranosyl-(1→2)-α-L-arabinopyranosyl]-hederagenin.

(3) Saponin C

Saponin C is a known substance (Phytochemistry, 20, 1939 (1981). That is, Saponin C is 3-O-[α-L-arabinofuranosyl-(1→3)-α-L-rhamnopyranosyl-(1→2)-α-L-arabinopyranosyl]-hederagenin.

(4) Preparation of Saponins A, B and C

Saponins A, B and C can be prepared from the mukurossi peel.

The preparation steps according to one embodiment of the invention are described in detail below.

The mukurossi peel, without defatting or after being defatted with the use of a conventional lipid-soluble organic solvent, is subjected to extraction with an extracting reagent selected from a lower aliphatic alcohol, particularly $C_1$-$C_4$ monohydric alcohol and a mixture of water with a lower aliphatic alcohol. The extract is conducted by normal phase chromatography using adsorbent (preferably silica gel) with the use of an eluant, which is a solvent mixture of an insoluble organic solvent (e.g., ethyl acetate, chloroform, n-butanol), an alcohol (e.g., methanol, ethanol) and water to obtain saponin fractions. The fractions are then subjected to purification operation such as recrystallization, if possible, to obtain the desired isolated saponin product.

3. Drug absorption adjuvant composition

The drug absorption adjuvant composition contains a galenical extract or a product isolated therefrom as described above That is, the drug absorption adjuvant composition may comprise either a single kind of a galenical extract or a product isolated therefrom or a mixture of plural kinds of such galenical extracts or isolated products. Alternatively such a composition may further contain optionally any pharmaceutically acceptable liquid or solid vehicle. As the dosage form, there may be included powders, pills, tablets, emulsions, capsules, species, granules, parvules, solutions (including also fluidextracts and syrups), troches, and any other form administrable orally or by insertion into the rectum.

The composition may be administered in any desired dosage, as long as the effect of promoting drug absorption can be recognized. Most saponin-containing galenicals are known in the art as starting materials for herb medicines, and therefore suitable levels of dosage are already empirically known. Thus, in the present invention, the optimum dosage for a given pharmacologically active substance to give a desired absorption improvement effect can easily be determined on the basis of such empirically known dosage levels. As described above, the extract utilized in the present invention has also a physiological activity well known in the art and it will sometimes be necessary to take such an activity into consideration in determining the dosage in the practice of the present invention. However, as a measure for producing a desirable drug absorption promoting effect, a galenical extract or a product isolated therefrom may be administered generally at a level of 2.5 to 250 mg, preferably 20 to 50 mg per dose for a human adult.

The drug absorption adjuvant composition according to the present invention is ordinarily prepared separately from the preparation of a pharmacologically active substance to be promoted in its absorption. In this case, the commercially available product will take the form of a kit comprising a preparation of the pharmaceutically active substance and a preparation of the absorption adjuvant composition. However, if desired, the composition can also be made into a preparation integrally combined with an objective pharmacologically active substance.

As mentioned above, triterpenoid saponins containing hederagenin as aglycone are obtained from various kinds of plants. But, it can be said that the pharmacological activity of a saponin depends greatly on the kinds of sapogenins as described, for example, in "Biologically Active Natural Substances" edited by Shoji Shibata, 418, 1978). Therefore, it may be possible to analogize that the saponins contained in the extracts of the starting materials other than the mukurossi peel having the drug absorption promoting effect of the present invention are triterpenoid saponins similarly as the above saponins A, B and C, and some of them may be triterpenoid saponins containing hederagenin as aglycone similarly as said saponins A, B and C.

4. Pharmacologically active substances

The pharmacologically active substances to be promoted in absorption with the use of a saponin-containing galenical extract or a product isolated from the extract are drugs to be administered orally or into the rectum, the concentrations of which in the blood are desirably held persistently for a long time at a level of minimal effective concentration in the blood or higher.

Examples of such pharmacologically active substances are β-lactam type antibiotics, especially penicillins and cephalosporins, and physiologically active peptides. Among these, typical examples are β-lactam type antibiotics, especially penicillins and cephalosporins as set forth below.

As penicillins, there are Ampicillin, Ciclacillin, Cloxacillin, Benzylpenicillin, Carbenicillin, Piperacillin, Mezolocillin, Sulbenicillin, Ticarcillin, Apalcillin, Amoxicillin, Hetacillin, Talampicillin and sodium salts thereof.

As cephalosporins, Cefalexin, Ceftezole, Cefapirin, Cefalotin, Cefoxitin, Cefmetazole, Cefazolin, Cefaloridine, Cefacetrile, Cefotiam, Ceforanide, Cephanone, Cefaclor, Cefadroxil, Cefatridine, Cefradine, Cefaloglycin, Cefoperazone (T-1551) and sodium salts thereof may be mentioned.

5. Experimental example (I): Galenical extract

Experimental method A

Rats weighing 180 to 220 g were anesthetized with 30 mg/kg of pentobarbital sodium and fixed by supination on a water bed made of a metal through which water regulated at a constant temperature of 39° C. was circulated. A duodenal loop of 10 cm length was prepared in a conventional manner with the point 1 cm under the pyloric part of the stomach as the starting point. Into the loop was injected a solution of ampicillin sodium and a galenical extract dissolved in a phosphate buffer of pH 6.5 in a proportion of 0.5 ml per 200 g of body weight of the rat. The rats were bled from jugular veins 10, 20, 40, 60, 90, 120, 180 and 240 minutes after injection and activity concentration in the blood in each case was measured according to biological assay.

That is, according to The Japan Antibiotic Drug Standards, using Bacillus subtilis as test microorganism, cultivation assay was performed by the paper disc method at 37° C. for 15 to 20 hours.

The composition of the solution had the following composition:
Ampicillin sodium: 20 mg/ml
Galenical extract: 2 mg/ml–20 mg/ml Examples according to the experimental method A are shown in Examples 1A through 4A.

Experimental method B

Rats weighing 200 to 230 g under anesthesia with ether were intubated with polyethylene tube (PE-10) at the femoral artery with ligation. The other end of PE-10 was passed subcutaneously to be led to the cervicodorsal part, at which it was drawn out of the skin and fixed with capping. After restoration of the vulnus at the operated portion (about 24 hours), each rat was provided for the experiment.

A solution having ampicillin sodium (5 mg/ml) and a galenical extract (1 mg/ml) dissolved in purified water was administered by means of a stomach probe in a proportion of 1 ml per 200 g of rat body weight, and the blood was sampled periodically with elapse of time for measurement of activity concentration according to biological assay.

The test microorganism used was Bacillus subtilis, and the assay was performed by the paper disc method according to The Japan Antibiotic Drug Standards.

An example according to the experimental method B is given in Example 5B.

EXAMPLE 1A

Table 1 shows the results obtained when using n-butanol extract of Bupleurum falcatum L.

TABLE 1

| Conc. of Bupleurum falcatum extract | Rat No. | Conc. of Pharmacologically Active Substance in Blood Concentration in Blood (μg titer/ml) | | | | | | | |
|---|---|---|---|---|---|---|---|---|---|
| | | 10 min. | 20 min. | 40 min. | 60 min. | 90 min. | 120 min. | 180 min. | 240 min. |
| 20 mg/ml | 1 | 6.9 | 17.5 | 18.4 | 14.2 | 9.0 | 4.1 | 2.5 | 2.1 |
| | 2 | 5.8 | 16.0 | 15.5 | 14.0 | 8.0 | 4.1 | 2.3 | 1.7 |
| 5 mg/ml | 1 | 3.2 | 9.0 | 9.0 | 6.3 | 4.7 | 3.3 | 1.5 | 1.0 |
| | 2 | 2.4 | 7.5 | 7.7 | 5.5 | 2.9 | 1.6 | 0.5 | 0.5 |
| 0 (Control) | 1 | 0.6 | 0.9 | 1.1 | 1.2 | 0.9 | 0.9 | 0.5 | 0.5 |

EXAMPLE 2A

Table 2 shows the results when a mukurossi peel extract TN-4-Bu was used in a concentration of 2 mg/ml.

TABLE 2

| Rat No. | Conc. of Pharmacologically Active Substance in Blood Concentration in Blood (μg titer/ml) | | | | | | | |
|---|---|---|---|---|---|---|---|---|
| | 10 min. | 20 min. | 40 min. | 60 min. | 90 min. | 120 min. | 180 min. | 240 min. |
| 1 | 3.8 | 12.0 | 19.2 | 17.1 | 14.5 | 12.7 | 8.7 | 7.7 |
| 2 | 5.7 | 20.4 | 23.0 | 18.4 | 17.6 | 14.5 | 11.3 | 7.7 |
| 3 | 3.5 | 11.2 | 14.0 | 12.4 | 7.6 | 5.3 | 3.7 | 3.8 |
| 4 | 9.4 | 16.5 | 14.3 | 8.5 | 4.7 | 2.6 | 1.2 | 0.5 |
| 5 (Control) | 0.6 | 0.9 | 1.1 | 1.2 | 0.9 | 0.9 | 0.5 | 0.5 |

EXAMPLE 3A

Table 3 shows the results when a mukurossi peel extract $TN-4-E_{3-5}$ was used in a concentration of 2 mg/ml.

TABLE 3

| Rat No. | Conc. of Pharmacologically Active Substance in Blood Concentration in Blood (μg titer/ml) | | | | | | | |
|---|---|---|---|---|---|---|---|---|
| | 10 min. | 20 min. | 40 min. | 60 min. | 90 min. | 120 min. | 180 min. | 240 min. |
| 1 | 10.3 | 22.1 | 27.5 | 20.0 | — | 10.3 | 7.1 | — |
| 2 | 5.4 | 14.5 | 19.7 | 18.1 | — | 10.9 | 9.2 | 8.1 |
| 3 | 13.6 | 20.6 | 24.9 | 22.0 | — | 14.4 | 11.1 | 11.0 |
| 4 | 6.3 | 15.4 | 19.2 | 17.6 | — | 4.3 | 3.7 | 3.1 |
| 5 (Control) | 0.6 | 0.9 | 1.1 | 1.2 | 0.9 | 0.9 | 0.5 | 0.5 |

EXAMPLE 4A

Table 4 shows the results when a mukurossi peel extract TN-4-E$_2$ was used in a concentration of 2 mg/ml.

TABLE 4

| | Conc. of Pharmacologically Active Substance in Blood | | | | | | | |
|---|---|---|---|---|---|---|---|---|
| | Concentration in Blood (μg titer/ml) | | | | | | | |
| Rat No. | 10 min. | 20 min. | 40 min. | 60 min. | 90 min. | 120 min. | 180 min. | 240 min. |
| 1 | 5.6 | 13.7 | 19.5 | 15.0 | — | 5.5 | 4.9 | — |
| 2 | 5.5 | 20.3 | 25.5 | 12.8 | — | 3.1 | 2.6 | 2.1 |
| 3 | 5.5 | 21.1 | 26.5 | 16.9 | — | 5.9 | 2.6 | 2.2 |
| 4 | 7.8 | 20.7 | 25.0 | 14.3 | — | 5.4 | 3.1 | 2.8 |
| 5 (Control) | 0.6 | 0.9 | 1.1 | 1.2 | 0.9 | 0.9 | 0.5 | 0.5 |

EXAMPLE 5B

TABLE 5

| | Conc. of Pharmacologically Active Substance in Blood | | | | | | | |
|---|---|---|---|---|---|---|---|---|
| | Concentration in Blood (μg titer/ml) | | | | | | | |
| Rat No. | 10 min. | 20 min. | 40 min. | 60 min. | 90 min. | 120 min. | 180 min. | 240 min. |
| 1 + | 0.4 | 0.9 | 2.0 | 1.7 | 1.0 | 0.6 | 0.4 | tr. |
| − (Control) | 0.4 | 0.8 | 1.2 | 0.8 | 0.3 | tr. | tr. | tr. |
| 2 + | 0.8 | 1.8 | 2.1 | 1.7 | 1.2 | 0.8 | 0.2 | tr. |
| − (Control) | 0.3 | 0.6 | 1.3 | 0.5 | tr. | tr. | tr. | tr. |

Note:
tr.: trace

In the above Examples, the extract samples were prepared according to the methods described below.

(1) *Bupleurum falcatum* L. extract 500 g of minces of a biennial *Bupleurum falcatum* L. was employed.

Extraction was performed for aliquots each of 50 g with 500 ml of methanol/50 g using a mixer at room temperature, and extraction was repeated three times for each aliquot. (Consequently, 500 g of *Bupleurum falcatum* L. was extracted with 15 liters of methanol.) The methanol layer was subjected to evaporation to obtain 122 g of a methanol extract. The methanol extract was suspended in 750 ml of water, and the suspension was extracted (defatted) twice with 750 ml of diethyl ether to obtain 3 g of an ether extract. In the second time extraction, an emulsion was formed and the emulsion was made into aqueous layers. These aqueous layers were extracted 5 times with n-butanol saturated with water (total quantity, 1.8 liter) and evaporated at 38° to 40° C. (to prevent decomposition of Bupleurum root saponin by heat) to produce 52 g of a butanol extract.

The butanol extract was lyophilized, and 3 g of the product was used as a sample for pharmacological test (this sample was hygroscopic).

(2) Mukurossi peel extract

Mukurossi peel (100 g) was broken into pieces by hand and defatted by dipping in cold benzene (room temperature, 400 ml×3 times).

The defatted galenical was extracted by dipping in hot methanol (70° C., 400 ml×5). The methanol extract layer was subjected to evaporation to produce 65.6 g of a methanol extract (TN-4-M). Of the methanol extract, 11.4 g was reserved for storage, and 54.3 g was suspended in 350 ml of water and extracted with ethyl acetate (300 ml×5 times). During this operation, the emulsion portion was formed into an aqueous layer. After evaporation of the ethyl acetate layer, there were obtained 1.26 g (TN-4-E) as the first extract, 0.64 g (TN-4-E$_2$) as the second extract, and 1.21 g (TN-4-E$_{3-5}$) as the third to fifth extracts, respectively, making a total of 3.11 g. The aqueous layer after extraction with ethyl acetate was further subjected to extraction with n-butanol saturated with water (300 ml×once), followed by evaporation of the butanol layer, to produce 16.42 g (TN-4-Bu).

Experimental example (II) Isolated saponin product (1) Extraction

Mukurossi peel (370 g) was broken into pieces by hand and defatted by dipping in cold methanol (room temperature, one liter). The defatted galenical was extracted by dipping in hot methanol (70° C., one liter×2). The methanol extract layer was subjected to evaporation to obtain 200 g of a methanol extract. Of the methanol extract, 140 g was reserved for storage, and 60.0 g was suspended in 200 ml of water and extracted with n-hexane. During this operation, in order to prevent emulsion formation, 8 ml of ethanol was added. After evaporation of the n-hexane layer, 290 mg of an extract was obtained. The aqueous layer after extraction with n-hexane was subjected to extraction with ethyl acetate (200 ml×6 times). The ethyl acetate layer was evaporated to produce 2.7 g of the first through the third extracts and 1.0 g of the fourth through the sixth extracts, respectively. The aqueous layer after extraction with ethyl acetate was further subjected to extraction with n-butanol saturated with water (200 ml×once), which step was followed by evaporation of the butanol layer to obtain 11.4 g of a butanol extract (TN-3-Bu).

(2) Isolation

The extract TN-3-Bu (11.4 g) prepared in the foregoing operation was subjected to column chromatography using a column of silica gel with an eluant of ethyl acetate-ethanol-water (15:2:0.8→15:3:1.2) to obtain fractions Nos. 1 through 50.

Evaporation of the solvent from the fraction No. 31 produced 350 mg of a residue, which was further subjected to recrystallization from methanol/ethyl acetate to obtain 110 mg of saponin A.

Evaporation of the solvent from the fractions Nos. 19 through 22 produced 1.32 g of a residue, which was subjected to chromatography through a column of silica gel with an eluant of ethyl acetate-ethanol-water (8:2:1) to obtain fractions Nos. 51 through 100. From 330 mg of the residue after evaporation of the solvent from the fractions Nos. 80 and 81, 270 mg of saponin B was obtained by recrystallization from a dilute methanol solution.

The residue (630 mg) obtained by evaporation of the solvent from the fractions Nos. 16, 18 and 19 was subjected to column chromatography using silica gel with an eluant of ethyl acetate-ethanol-water (16:2:1) to obtain fractions Nos. 101 through 110. The residue (170 mg) obtained by evaporation of the solvent from the fraction No. 17 was also subjected to chromatography through a silica gel column with an eluant of ethyl acetate-ethanol-water (45:10:1) to obtain fractions Nos. 111 through 120. From the residue after evaporation of the solvent from the fractions Nos. 103 and 112, there was obtained 210 mg of saponin C.

(3) Pharmacological tests

Experimental method A was repeated except that saponins A, B and C were respectively used in a concentration of 5 mg/liter in place of the galenical extract in a solution to be administered.

Examples according to the above experimental method are shown in the following Examples 6, 7 and 8. In each of the Examples, there was no damage of mucosa (e.g. mucosa ablation) or abnormality such as hemorrhagic spot by observation of the duodenum employed in the experiment. This may be ascribed to low acute toxicity of the drug absorption promoter of the present invention, as can readily be understood from the fact that the galenicals used in the present invention have been widely accepted as herb medicines or the like.

EXAMPLE 6

Table 6 shows the results when isolated saponin A was used.

TABLE 6

| Rat No. | Conc. of Pharmacologically Active Substance in Blood | | | | | | |
|---|---|---|---|---|---|---|---|
| | Concentration in Blood (μg titer/ml) | | | | | | |
| | 10 min. | 20 min. | 40 min. | 60 min. | 90 min. | 120 min. | 180 min. |
| 1 | 2.08 | 6.23 | 6.64 | 6.79 | 5.41 | 4.58 | 2.34 |
| 2 | 0.90 | 3.91 | 4.43 | 4.46 | 2.47 | 2.07 | 1.15 |
| 3 | 4.93 | 7.02 | 7.32 | 5.15 | 2.78 | 2.34 | 2.85 |
| 4 | 1.06 | 2.22 | 3.93 | 4.35 | 3.60 | 2.67 | 2.53 |
| 5 | 1.35 | 4.06 | 3.52 | 2.03 | 1.10 | 0.89 | 0.57 |
| 6 | 2.01 | 5.63 | 5.15 | 3.79 | 2.88 | 2.07 | 2.01 |
| (Control) | 0.55 ± 0.04 | 0.89 ± 0.07 | 1.28 ± 0.09 | 1.41 ± 0.16 | 1.42 ± 0.04 | 1.25 ± 0.12 | 0.85 ± 0.11 |

EXAMPLE 7

Table 7 shows the results when isolated saponin B was used.

TABLE 7

| Rat No. | Conc. of Pharmacologically Active Substance in Blood | | | | | | |
|---|---|---|---|---|---|---|---|
| | Concentration in Blood (μg titer/ml) | | | | | | |
| | 10 min. | 20 min. | 40 min. | 60 min. | 90 min. | 120 min. | 180 min. |
| 1 | 3.18 | 6.34 | 4.08 | 2.62 | 1.61 | 1.04 | 1.11 |
| 2 | 3.18 | 9.25 | 8.63 | 6.23 | 2.58 | 1.72 | 1.19 |
| 3 | 1.73 | 4.63 | 5.98 | 4.28 | 3.07 | 2.70 | 3.14 |
| (Control) | 0.55 ± 0.04 | 0.89 ± 0.07 | 1.28 ± 0.09 | 1.41 ± 0.16 | 1.42 ± 0.04 | 1.25 ± 0.12 | 0.85 ± 0.11 |

EXAMPLE 8

Table 8 shows the results when an isolated saponin C was used.

TABLE 8

| Rat No. | Conc. of Pharmacologically Active Substance in Blood | | | | | | |
|---|---|---|---|---|---|---|---|
| | Concentration in Blood (μg titer/ml) | | | | | | |
| | 10 min. | 20 min. | 40 min. | 60 min. | 90 min. | 120 min. | 180 min. |
| 1 | 2.2 | 5.97 | 5.44 | 4.27 | 3.00 | 2.07 | 1.48 |
| 2 | 1.15 | 4.11 | 5.28 | 5.32 | 3.92 | 3.63 | 3.08 |
| 3 | 0.40 | 2.44 | 3.38 | 3.75 | 2.28 | 2.06 | 1.79 |
| Control | 0.55 ± 0.04 | 0.89 ± 0.07 | 1.28 ± 0.09 | 1.41 ± 0.16 | 1.42 ± 0.04 | 1.25 ± 0.12 | 0.85 ± 0.11 |

(4) Suppository tests (Examples 11-15)

The effectiveness of the saponins A, B and C when they were formulated into suppositories was tested in a method similar to the above Experimental method A.

Thus, rats weighing 180 to 220 g were anesthetized with 30 mg/kg of pentobarbital sodium and fixed by supination on a water bed made of a metal through which water regulated at a constant temperature of 39° C. was circulated. A suppository in a proportion of 1 g/kg of body weight of the rat was inserted through the anus and pushed by a glass bar until it reached the connecting point of the pubes.

The suppositories tested had the following compositions:

Ampicillin sodium: 50 mg/kg-rat,
Saponin A, B or C: 0.5–2 mg/kg-rat, and
Vehicle*: remainder for giving 1 mg of suppository/kg-rat.

*Witepsol® produced by Dynamit Novel A.G.

The kind of the saponin and the amount thereof used in each of the examples were as follows:

Example 11: Saponin A 0.5 mg/kg-rat
Example 12: Saponin A 1.0 mg/kg-rat
Example 13: Saponin A 2.0 mg/kg-rat
Example 14: Saponin B 1.0 mg/kg-rat
Example 15: Saponin C 1.0 mg/kg-rat Each of the rats to which a suppository was administered as mentioned above was bled from jugular veins at predetermined points of time after the administration shown in the Table 8A appearing hereinbelow and the concentration of the ampicillin sodium in the sample blood was measured according to biological assay.

Thus, the assay was performed by the paper disc method according to The Japan Antibiotic Drug Standards using Bacillus subtilis as the test microorganism.

The results of the above assay are summarized in the following Table 8A.

TABLE 8A

Conc. of Pharmacologically Active Substance in Blood

Concentration in Blood (μg/ml)

|  | 5 min. | 10 min. | 15 min. | 35 min. | 60 min. | 100 min. |
|---|---|---|---|---|---|---|
| Example 11 (n = 6) | 5.91 ± 3.08 | 8.13 ± 3.29 | 7.57 ± 2.36 | 4.28 ± 1.89 | 2.49 ± 1.38 | 0.92 ± 0.90 |
| Example 12 (n = 6) | 8.27 ± 3.37 | 12.03 ± 3.20 | 10.41 ± 3.06 | 5.71 ± 1.49 | 3.16 ± 0.93 | 1.85 ± 0.64 |
| Example 13 (n = 4) | 13.56 ± 3.12 | 14.43 ± 3.48 | 12.61 ± 2.96 | 6.30 ± 0.97 | 2.76 ± 0.40 | 1.02 ± 0.11 |
| Control (n = 8) | 3.12 ± 1.66 | 3.98 ± 1.89 | 3.74 ± 1.80 | 1.91 ± 0.89 | 0.93 ± 0.54 | trace |

|  | 10 min. | 20 min. | 30 min. | 50 min. | 100 min. | 150 min. |
|---|---|---|---|---|---|---|
| Example 14 (n = 3) | 10.73 ± 5.42 | 9.39 ± 5.27 | 6.30 ± 3.22 | 3.16 ± 0.87 | 1.58 ± 0.91 | 1.28 ± 1.21 |
| Example 15 (n = 4) | 11.72 ± 4.57 | 9.33 ± 0.88 | 6.30 ± 1.22 | 3.37 ± 1.31 | 1.15 ± 0.53 | 0.54 ± 0.37 |

The saponins A, B and C as prepared above have physical and chemical properties as shown in Table 9. The results of $^{13}$C-NMR are shown in Table 10.

TABLE 9

|  | Saponin A | Saponin B | Saponin C |
|---|---|---|---|
| Appearance | White powder | White powder | White powder |
| m.p. | 227–230° C. (MeOH—EtOAc) | 239–240° C. (aq. MeOH) | indefinite |
| Optical Rotation | $[\alpha]_D^{15°} = +12.1°$ (c = 1.03, MeOH) | $[\alpha]_D^{18°} = +5.96°$ (c = 1.36, MeOH) | $[\alpha]_D^{15°} = -14.3°$ (c = 0.58, MeOH) |
| IR $\nu_{max}^{KBr}$ cm$^{-1}$ |  |  |  |
| —COOH | 1690 | 1690 | 1690 |
| —OH | 3400 | 3400 | 3400 |
| EI-Mass (m/z) | 259 (ara.) | 259 (xyl.) | 259 (terminal ara) |
| (acetate) | 489 (rha-ara) | 489 (rha-xyl) 705 (ara-rha-xyl) | 489 (rha-ara) |

TABLE 10

|  | Saponin A | Saponin B | Saponin C | Saponin P$_G$ (Akebia quinata Decne) |
|---|---|---|---|---|
| aglycone C-1 | 38.9 | 38.9 | 38.8 | 38.8 |
| 2 | 26.1 | 26.1 | 26.1 | 26.1 |
| 3 | 81.2 | 80.9 | 81.3 | 80.9 |
| 4 | 43.5 | 43.5 | 43.4 | 43.4 |
| 5 | 47.7 | 47.5 | 47.8 | 47.5 |
| 6 | 18.2 | 18.4 | 18.3 | 18.3 |
| 7 | 33.2 | 33.2 | 33.2 | 33.2 |
| 8 | 39.7 | 39.6 | 39.7 | 39.6 |
| 9 | 48.1 | 48.1 | 48.1 | 48.0 |
| 10 | 36.8 | 36.8 | 36.8 | 36.8 |
| 11 | 23.7 | 23.7 | 23.7 | 23.7 |
| 12 | 122.5 | 122.3 | 122.6 | 122.3 |
| 13 | 144.6 | 144.4 | 144.7 | 144.4 |
| 14 | 42.0 | 42.0 | 42.0 | 42.0 |
| 15 | 28.2 | 28.2 | 28.3 | 28.1 |
| 16 | 23.7 | 23.7 | 23.7 | 23.7 |
| 17 | 46.5 | 46.5 | 46.6 | 46.5 |
| 18 | 42.0 | 41.8 | 42.0 | 41.8 |
| 19 | 46.5 | 46.5 | 46.6 | 46.5 |
| 20 | 30.9 | 30.8 | 30.9 | 30.8 |
| 21 | 34.2 | 34.1 | 34.2 | 34.2 |
| 22 | 33.2 | 33.2 | 33.2 | 33.2 |
| 23 | 64.1 | 63.9 | 64.1 | 64.0 |
| 24 | 14.0 | 14.1 | 13.9 | 14.0 |
| 25 | 16.0 | 16.1 | 16.0 | 16.0 |
| 26 | 17.4 | 17.4 | 17.4 | 17.4 |
| 27 | 26.1 | 26.1 | 26.1 | 26.1 |
| 28 | 180.1 | 179.8 | 180.2 | 179.7 |
| 29 | 33.2 | 33.2 | 33.2 | 33.2 |
| 30 | 23.7 | 23.7 | 23.7 | 23.7 |
| ara 1' | 104.4 | 104.3 | 104.4 | 104.2 |
| 2' | 75.2 | 75.4* | 75.4 | 75.3 |
| 3' | 74.6 | 74.8 | 74.6 | 74.7 |
| 4' | 69.3 | 69.4 | 69.4 | 69.4 |
| 5' | 65.8 | 65.9 | 65.8 | 65.8 |
| rha 1" | 101.2 | 101.1 | 101.2 | 101.0 |
| 2" | 71.7 | 71.7 | 71.6 | 71.7 |
| 3" | 82.5 | 82.6 | 82.2 | 82.6 |
| 4" | 72.9 | 72.7 | 72.3 | 72.6 |
| 5" | 69.3 | 69.4 | 69.4 | 69.4 |
| 6" | 18.2 | 18.3 | 18.3 | 18.3 |
| terminal monose | ara | xyl | ara(fur) | xyl |
| 1''' | 107.0 | 107.1 | 110.8 | 107.0 |
| 2''' | 72.9 | 75.2* | (79.2) | 75.3 |
| 3''' | 74.3 | 78.1 | (78.7) | 78.0 |
| 4''' | 69.3 | 70.8 | 87.2 | 70.8 |
| 5''' | 66.9 | 67.1 | 62.7 | 67.1 |

On the basis of the results of $^{13}$C-NMR, saponins A, B and C were identified to have structures as determined according to the following procedure.

From the $^{13}$C-NMR as shown above, each compound was found to have three sugars since the number of anomers was three. Subsequently, each compound was subjected to acid hydrolysis, and the sugars were identified by TLC and GLC to obtain the results shown below.

TABLE 11

| Saponin A | arabinose, rhamnose |
|---|---|
| Saponin B | arabinose, rhamnose, xylose |

TABLE 11-continued

| | |
|---|---|
| Saponin C | arabinose, rhamnose |

Aglycone contained in each saponin was found to be hederagenin, as determined by $^{13}$C-NMR.

The measurement of FD-MS in which m/z 905 (M+Na)+ appeared suggested that saponin A has two molecules of arabinose and one molecule of rhamnose bonded to hederagenin.

On the other hand, enzymatic partial hydrolysis was accomplished with the use of crude pectinase I, and prosapogenin (called prosapogenin A) was separated by silica gel column chromatography. From measurement of $^{13}$C-NMR, it was found to be completely identical with saponin Po (Kawasaki et al, Chem. Pharm. Bull. 24, 1021 (1976)) obtained from peels of Akebia quinata Decne. Table 12 shows comparison between the data of both compounds.

TABLE 12

| | Pro-Sapoqenin A | Saponin Po (Akebia quinata Decne) |
|---|---|---|
| aglycone C-1 | 38.9 | 38.9 |
| 2 | 26.1 | 26.1 |
| 3 | 81.1 | 81.0 |
| 4 | 43.5 | 43.4 |
| 5 | 47.7 | 47.7 |
| 6 | 18.2 | 18.1 |
| 7 | 32.8 | 32.8 |
| 8 | 39.7 | 39.7 |
| 9 | 48.1 | 48.1 |
| 10 | 36.9 | 36.8 |
| 11 | 23.8 | 23.8 |
| 12 | 122.7 | 122.5 |
| 13 | 144.7 | 144.7 |
| 14 | 42.1* | 42.1 |
| 15 | 28.3 | 28.3 |
| 16 | 23.8 | 23.8 |
| 17 | 46.6 | 46.6 |
| 18 | 42.0* | 42.1 |
| 19 | 46.6 | 46.4 |
| 20 | 31.0 | 30.9 |
| 21 | 34.2 | 34.2 |
| 22 | 33.2 | 33.2 |
| 23 | 64.0 | 63.9 |
| 24 | 14.0 | 13.9 |
| 25 | 16.1 | 16.0 |
| 26 | 17.5 | 17.4 |
| 27 | 26.1 | 26.1 |
| 28 | 180.2 | 180.1 |
| 29 | 33.2 | 33.2 |
| 30 | 23.8 | 23.8 |
| ara C-1' | 104.2 | 104.3 |
| 2' | 75.8 | 75.8 |
| 3' | 74.4 | 74.6 |
| 4' | 69.1 | 69.2 |
| 5' | 65.3 | 65.5 |
| rha C-1" | 101.5 | 101.6 |
| 2" | 72.3 | 72.5 |
| 3" | 72.3 | 72.3 |
| 4" | 74.1 | 74.1 |
| 5" | 69.7 | 69.7 |
| 6" | 18.4 | 18.5 |

Thus, prosapogenin A was identified to be hederagenin 3-O-α-L-rha.pyra-(1→2)-α-L-ara.pyranoside. The terminal sugar cleaved by enzymatic partial hydrolysis was identified by TLC and GLC to be arabinose.

From the above results, peaks of $^{13}$C-NMR were assigned as shown in Table 10, and saponin A was identified to have the above structural formula.

Saponin B was found to exhibit $^{13}$C-NMR which was completely identical with that of saponin $P_G$ of Akebia quinata Decne (which is also listed in Table 10) as reported by R. Higuchi et al (Chem. Pharm. Bull. 24, 1021 (1976)) and therefore identified to have the above structural formula.

Saponin C, after enzymatic partial hydrolysis, exhibits the spot with an $R_f$ value identical with that of said prosapogenin A on TLC. Also from the fact that terminal cleavage occurs with naringinase or hesperiginase similarly as pectinase I, saponin C was found to have terminal sugars different from saponin A.

On the other hand, for investigation on the location of sugars bonded, permethylation was conducted according to the Hakomori method (J. Biochem. (Tokyo) 55, 205 (1964)), which was followed by methanolysis and GLC, whereby the presence of arabinose as terminal sugar was confirmed.

From the above results, saponin C was found to have the above structural formula.

What we claim is:

1. A method for enhancing the absorption by an animal of a β-lactam type antibiotic selected from the group consisting of penicillins and cephalosporins, which comprises orally or rectally administering to an animal in need of said antibiotic the antibiotic and a safe and effective amount of a saponin obtained from a plant selected from the group consisting of:

(a) *Akebia quinata* decne. or plants belonging to the same family (Lardizabalaceae);

(b) *Fatsia japonica* Decne. et Pianch;

(c) *Caulophyllum robustum* Maxim.;

(d) *Hedera rhombea* Bean;

(e) *Clematis chinensis* Osbeck;

(f) *Pulsatilla cernua* Spreng;

(g) *Sapindus mukurossi* Gaertn.;

(h) *Panax japonicum* C. A. Meyer;

(i) *Glycyrrhiza glabra* L.var. glandulifera Regel et Herber, *Glycyrrhiza uralensis* Fisher or plants belonging to the same family (Leguminosae);

(j) *Polygala senega* L. or *Polygala senega* L. var. Latifolia Torrey et Gray;

(k) Platycodon grandiflorum A.D.C.;

(l) *Polygala tenuifolia* Willd.;

(m) *Achyranthes fauriei* Lev. et Van or *Achyranthes bidentata* Blume;

(n) *Cyclamen europaenum*;

(o) *Primula officinalis*;

(p) *Bupleurum falcatum* L. or its varieties (Umbelliferae);

(q) *Panax ginseng* C. A. Meyer;

(r) *Panax notoginseng* Burkill; and (s) *Panax quinquefolium* L.

2. A method according to claim 1 wherein the saponin is administered in a dosage of 2.5 to 250 mg per dose for a human adult.

3. The method according to claim 1 wherein the saponin is obtained from *Sapindus mukurossi* Gaertn.

4. The method according to claim 1 wherein the saponin is obtained from *Bupleurum falcatum* L. or Umbelliferae.

5. The method according to claim 1 wherein the saponin is a triterpenoid saponin of the formula

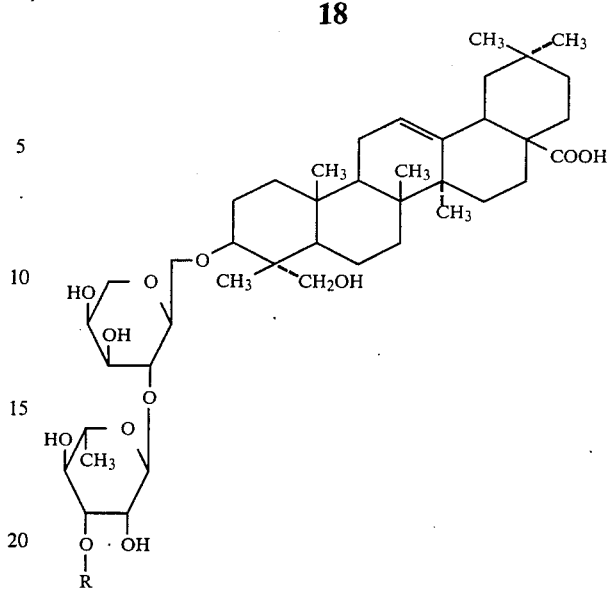

wherein R is

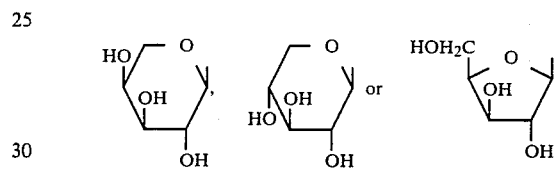

6. The method of claim 1 wherein the antibiotic is ampicillin and the saponin is selected from the group consisting of:
(a) 3-O-[α-L-arabinopyranosyl-(1→3)-α-L-rhamnopyranosyl-(1→2)-α-L-arabinopyranosyl]-hederagenin;
(b) 3-O-[β-D-xylopyranosyl-(1→3)-α-L-rhamnopyranosyl-(1→2)-α-L-arabinopyranosyl]-hederagenin; and
(c) 3-O-[α-L-arabinofuranosyl-(1→3)-α-L-rhamnopyranosyl-(1→2)-α-L-arabinopyranosyl]-hederagenin.

* * * * *